United States Patent

Inoue et al.

[11] 4,216,311
[45] Aug. 5, 1980

[54] PROCESS FOR PRODUCING A GLYCOLIPID METHYL ESTER

[75] Inventors: Shigeo Inoue, Saitama; Yoshiharu Kimura, Ichikawa; Manzo Kinta, Funabashi, all of Japan

[73] Assignee: Kao Soap Co., Ltd., Tokyo, Japan

[21] Appl. No.: 961,555

[22] Filed: Nov. 17, 1978

[30] Foreign Application Priority Data

Feb. 17, 1978 [JP] Japan .................................. 53-17401

[51] Int. Cl.² ........................ C07H 15/06; C07H 3/04
[52] U.S. Cl. ...................................... 536/115; 536/4; 536/116; 536/119
[58] Field of Search .................... 536/4, 115, 116, 119, 536/120

[56] References Cited

U.S. PATENT DOCUMENTS

| | | | |
|---|---|---|---|
| 2,602,789 | 7/1952 | Schwartz et al. | 536/116 |
| 2,931,797 | 4/1960 | Gibbons et al. | 536/116 |
| 2,992,082 | 7/1961 | Ownby et al. | 536/119 |
| 3,585,185 | 6/1971 | Levis, Jr. et al. | 536/116 |
| 3,631,025 | 12/1971 | Martin | 536/119 |
| 3,634,397 | 1/1972 | Tompson et al. | 536/119 |
| 4,011,389 | 3/1977 | Langdon | 536/120 |

*Primary Examiner*—Johnnie R. Brown
*Attorney, Agent, or Firm*—Oblon, Fisher, Spivak, McClelland & Maier

[57] ABSTRACT

A glycolipid methyl ester represented by the formula (I),

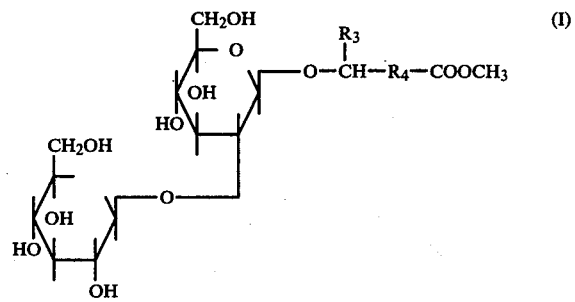

wherein $R_3$ represents a hydrogen atom or a methyl group, and $R_4$ represents a saturated or unsaturated hydrocarbon group having 12 to 16 carbon atoms when $R_3$ is a hydrogen atom, and $R_4$ represents a saturated or unsaturated hydrocarbon group having 11 to 15 carbon atoms when $R_3$ is a methyl group, is produced by adding at least one polyhydric alcohol represented by the formula (III) or (IV),

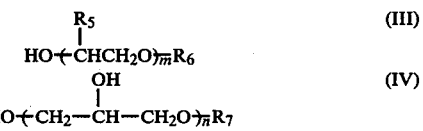

wherein $R_5$ represents a hydrogen atom or a methyl group, $R_6$ and $R_7$ represent a hydrogen atom or an alkyl group having 1 to 5 carbon atoms, and m and n represent integers from 1 to 6, to hydrated Sophorolipid, removing water by distillation under reduced pressure, and subjecting the resulting Sophorolipid-polyhydric alcohol system to methanolysis and methylation by reaction with methanol in the presence of a strong acid.

7 Claims, No Drawings

PROCESS FOR PRODUCING A GLYCOLIPID METHYL ESTER

BACKGROUND OF THE INVENTION

1. Field of the Invention

This invention relates to glycolipid methyl esters and in particular to a process for producing a glycolipid methyl ester having surface activity and wax-like properties and represented by formula (I),

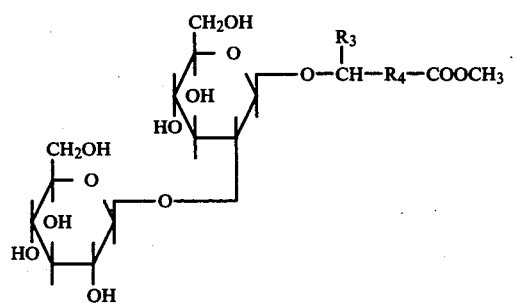

wherein $R_3$ represents hydrogen or methyl, $R_4$ represents a saturated or unsaturated hydrocarbon group having 12 to 16 carbon atoms when $R_3$ is a hydrogen atom, and $R_4$ represents a saturated or unsaturated hydrocarbon group having 11 to 15 carbon atoms when $R_3$ is a methyl group.

2. Description of the Prior Art

Higher fatty acids esters of sucrose (popular name: sugar esters) and higher fatty acid esters of anhydrosorbitol (popular name: Span) have been widely used in the field of surface active agents, particularly as emulsifying agents. Such known esters are formed via the ester bonding between the hydroxy group of the sugar moiety and the higher fatty acid, and the surface activities of these esters are regulated depending on their ester values. Selective esterification of sugar at its desired position or positions is nearly impossible because many hydroxy groups exist in the sugar structure. In this situation, therefore, only mixtures of various ester isomers are utilized on an industrial basis. The hydrophilic properties of these esters significantly decrease as the ester values increase because the esters are formed by esterification of the hydrophilic and hydroxy groups of the sugar. Consequently, much difficulty is encountered with the emulsifying processes. Another problem is that the esters are chemically unstable because the ester bond of the hydroxy groups in the sugar and higher fatty acid is more easily hydrolyzed than that of the common fatty alcohol esters.

It has been reported by J. F. T. Spencer et al [Canadian Journal of Chemistry, 39, 846 (1961)] that a great quantity of Sophorolipid is produced by culturing *Torulopsis bombicola*.

Sophorolipid is a mixture of the compounds represented by the formulas (IIa) and (IIb),

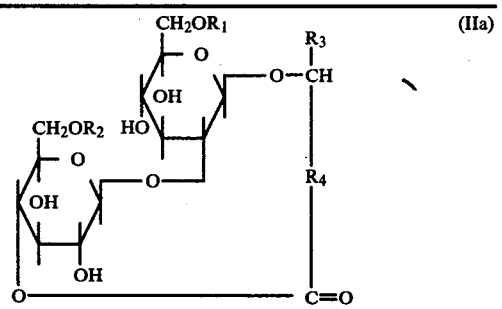

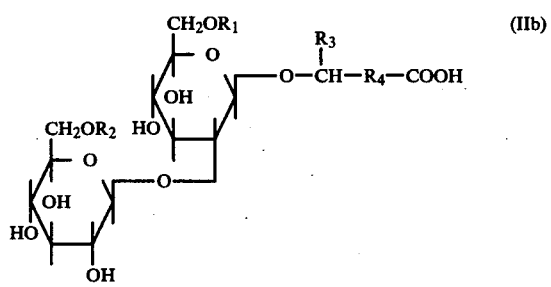

| | |
|---|---|
| IIa-1: | $R_1 = R_2 = COCH_3$ |
| IIa-2: | $R_1 = COCH_3, R_2 = H$ |
| IIa-3: | $R_1 = H, R_2 = COCH_3$ |
| IIa-4: | $R_1 = R_2 = H$ |
| IIb-1: | $R_1 = R_2 = COCH_3$ |
| IIb-2: | $R_1 = COCH_3, R_2 = H$ |
| IIb-3: | $R_1 = H, R_2 = COCH_3$ |
| IIb-4: | $R_1 = R_2 = H$ | wherein $R_3$ and $R_4$ in formulas (IIa) and (IIb) are the same as defined above.

As can be seen from formulas (IIa) and (IIb), Sophoropilid is a mixture of many glycolipids, and its basic structure is that of a [(2′-O-β-D-glycopyranosyl-β-D-glycopyranosyl)oxy]-alkane acid or alkene acid which is obtained via the glycoside bonding between Sophorose and a long-chain fatty acid having a hydroxy group at the ω or ω-1 position.

The compound of the present invention possesses structural features which cannot be found in the conventional glycolipid-type surface active agents and which are characterized by the fact that a stable glycoside bond is formed by the hyroxyfatty acid and sugar and that the end group of the alkyl or alkenyl group is a reactive carboxyl group. The compound is higher in chemical stability than those having the conventional ester bonds because the hydrophobic alkyl or alkenyl group is linked to the hydrophilic group is sugar via the glycoside bond. Moreover, since the alkyl or alkenyl group having hydrophobic properties is occupied at its end by the reactive carboxyl group, it is possible to produce glycolipids possessing surface-active and wax-like properties which have wide application by modification of only the carboxyl group without the hydroxy group of the sugar moiety chemically modified.

However, the production of the compound of formula (I) from Sophorolipid obtained by fermentation involves some problems. Namely, Sophorolipid cannot be used as a starting material because it is a mixture of many homologs having a lactone ring, a free carboxyl group, acetyl groups and the like as shown in formulas (IIa) and (IIb). Accordingly, the compound of the formula (IIb-4) should be first produced by eliminating the acetyl groups and releasing the carboxyl group without destruction of the carbon framework. The compound of formula (IIb-4) is a highly viscous substance peculiar to a sugar compound, and therefore, can only be obtained with much difficulty by means of any conventional method.

When Sophorolipid is forcibly dispersed in water and an acid or alkali is added to the resulting suspension in an amount necessary for normal hydrolysis of the ester bond, a part of the deacetylated or deacylated compound, which is subject to partial hydrolysis, acts as an emulsifying agent and incorporates the unreacted substances into micelles which protects them against continued attack by the remaining acid or alkali, thereby resulting in incompleted hydrolytic reaction.

For instance, the reaction proceeds only to an extent of about 50%, even if a given amount of potassium hydroxide (0.25 part per one part of Sophorolipid) is added to an aqueous solution containing 20% of Sophorolipid and the resulting solution is hydrolyzed with heating for 6 hours. When hydrochloric acid is used in an amount of 5% instead of the alkali catalyst, hydrolysis is as incomplete as in the case where the alkali catalyst is employed. Moreover, partial cleavage of the glycosyl ether bond results and damage to the basic structure occurs.

If the reaction is completed under the above conditions, potassium hydroxide should be used in an amount of 0.25 part per one part of Sophorolipid, which amount is extremely great, and it is nearly impossible to separate the formed compound of the formula (IIb-4) from the reaction solution by any industrially acceptable process. That is, the compound of the formula (IIb-4) is readily soluble in water, but can be only dissolved in lower alcohols such as methanol and ethanol, or special expensive organic solvents such as pyridine, dimethylsulfoxide and dimethylformamide, which would create a serious obstacle to safety. The compound of the formula (IIb-4) has a viscosity of more than 100,000 cps at room temperature. Moreover, since the potassium acetate formed at the same time is also readily soluble in water and alcohols, it is necessary to forcibly eliminate water and extract the potassium acetate with any one of the above nitrogen-containing solvents, and subsequently distill off the solvent in order to separate the compound of formula (IIb-4). This process is unacceptable from an industrial standpoint. It is not impossible but very difficult to obtain the compound of the present invention by reacting the free carboxyl group of the compound having the formula (IIb-4) with methanol because the compound of the formula (IIb-4) has a high viscosity. Another reason is that since there is no proper solvent capable of dissolving the compound, the glycosyl ether bond is cleaved under strongly acidic conditions.

With the above-noted difficulties in mind, a study has been conducted in which it has been found that non-hydrous Sophorolipid having a low viscosity can be obtained by adding a small amount of a polyhydric alcohol represented by formulas (III) or (IV),

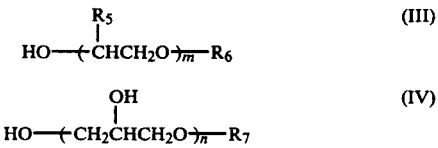

wherein $R_5$ represents a hydrogen atom or a methyl group, $R_6$ and $R_7$ represent a hydrogen atom or an alkyl group having 1 to 5 carbon atoms, and m and n represent integers from 1 to 6, to hydrated Sophorolipid which is a fermentation product of *Torulopsis bombicola*, and distilling off water under reduced pressure by application of heat. This discovery is the subject matter of co-pending application Ser. No. 928,964.

Further studies have been conducted for a method of producing a highly purified compound of the formula (I) from the reaction-completed mixture of Sophorolipid having a low viscosity and the polyhydric alcohol merely by distilling off solvent by subjecting the mixture to a methanolysis reaction by adding methanol and an acid to the mixture to deacetylate and cleave the lactone ring, and at the same time, methylate the free carboxy group. As a result, it has been found that the above reaction proceeds highly advantageously and that a compound of a high purity of the formula (I) can be obtained in a good yield merely by distilling off the solvent from the reaction complete mixture.

SUMMARY OF THE INVENTION

This invention provides a process for producing a glycolipid methyl ester of the formula (I), which comprises adding at least one polyhydric alcohol represented by formulas (III) or (IV) to hydrated Sophorolipid, removing water by distallation under reduced pressure, and subjecting the resulting Sophorolipid-polyhydric alcohol system to methanolysis and methylation reactions by reaction with methanol in the presence of a strong acid.

DETAILED DESCRIPTION OF THE PREFERRED EMBODIMENTS

Sophorolipid which is used in the present invention is hydrated Sophorolipid obtained by the fermentation of *Torulopsis bombicola* by any conventional method.

Suitable polyhydric alcohols which are useful in the invention include, for example, ethyleneglycol, ethyleneglycol monomethylether, ethyleneglycol monoethylether, ethyleneglycol monopropyl ether, diethyleneglycol, diethyleneglycol monomethyl ether, diethyleneglycol monoethyl ether, diethyleneglycol monobutyl ether, polyethyleneglycol having an average molecular weight of 150 to 280, propyleneglycol, dipropyleneglycol, tripropyleneglycol, tetrapropyleneglycol, pentapropyleneglycol, hexapropyleneglycol, propyleneglycol monomethyl ether, propyleneglycol monoethyl ether, propyleneglycol monopropyl ether, propyleneglycol monobutyl ether, dipropyleneglycol monomethyl ether, dipropyleneglycol monoethyl ether, tripropyleneglycol monomethyl ether and the like represented by the formula (III), and, for example, glycerine, polyglycerine, block-polymers of ethylene glycol and propyleneglycol and the like represented by formula (IV). The polyhydric alcohols can be used singly or in combination.

In practising the present invention, a polyhydric alcohol is first added to hydrated Sophorolipid, and water is exhaustively distilled off by means of any conventional topping apparatus. At the same time, any impurities having an offensive smell and a lower boiling point which are contained in the raw material are removed by distillation. It is preferable to add the polyhydric alcohol in an amount ranging from 1 to 10% in terms of its weight ratio to hydrated Sophorolipid.

The thus obtained Sophorolipid-polyhydric alcohol mixture does not contain water and any impurities having an offensive smell, and is easily dissolved in methanol. The Sophorolipid-polyhydric alcohol mixture is then dissolved in a doubled amount of methanol and reacted in the presence of a strong acid.

The use of an alkaline agent instead of an acid causes the formation of 30 to 40% by weight of the free carboxylic acid because of the presence of the compound of the formula (IIb) in Sophorolipid which amounts of 30 to 40% by weight, and 60 to 70% by weight of the methyl ester which results from cleavage of the lactone ring. Consequently, it is not preferable to conduct the reaction in the presence of an alkali.

Methanolysis barely proceeds hardly with the use of a weak acid such as phosphoric acid. A strong acid such as hydrochloric acid, sulfuric acid or nitric acid rapidly deacylates and cleaves the lactone ring, but the glycosyl ether bond is attacked under normal conditions for methylation whereby the basic structure is damaged. Because of these disadvantages, an attempt has been made to find better reaction conditions under which alcoholysis and methylation are perfectly completed without the glycosyl ether bond being damaged. In the studies leading to this invention, it has been found that the reaction proceeds advantageously with a strong acid such as hydrochloric acid, sulfuric acid or nitric acid in a concentration ranging from 0.05 to 0.50 N at a temperature of less than 45° C., and produces a single glycolipid methyl ester of the formula (I). It is to be noted that cleavage of the glycosyl ether bond is induced by using a strong acid at a concentration more than 0.50 N and that such cleavage proceeds rapidly at a reaction temperature above 45° C.

The reaction is conducted with stirring for about 90 minutes, and the resulting mixture is subjected to thin layer chromatography. The reaction is regarded as being completed when only one Sophorolipid spot is observed on the chromatogram.

After being allowed to cool to room temperature, the reaction solution is neutralized with sodium hyroxide, potassium hyroxide or an alkali metal methylate. The neutral salt which forms is removed by filtration, and the methyl acetate produced from the mother liquor and excessive methanol are removed by distillation under normal pressure, thereby yeilding a glycolipid methyl ester of the formula (I).

As described above, the glycolipid methyl ester obtained by the process of the present invention has both surface activity and wax-like properties and exhibits the following characteristics in comparison with the sugar esters of the conventional typical glycolipid-type surface active agents:

(1) The glycolipid methyl ester can be converted into a variety of glycolipid esters by ester interchange with alcohols. Among the sugar esters, the monoester is about 18 to 14, the diester, about 7 and the triester, about 3 to 4, respectively, in their HLB values. The HLB value variation is relatively small in the sugar esters. On the other hand, the glycolipid methyl ester has an HLB value of about 35, while the oleyl ester has a value of 6. Thus, various glycolipid esters having a wide range of HLB values can be obtained by changing the number of carbon atoms of the alcohols.

(2) While the surface tension is of the same degree in both types of compound, the surface tension of the glycolipid ethyl ester is about twice as high in forming power as the sugar ester (monooleate). Moreover, the glycolipid ethyl-ester is also superior as a detergent than the sugar ester.

(3) In terms of emulsifying ability, both types of compound give different emulsions. The glycolipid methyl ester forms a homogeneous emulsion containing extremely fine particles and also possesses the same emulsifying ability as the sugar ester in an amount of less than half the amount of the sugar ester.

(4) The glycolipid methyl ester has good miscibility with various fats and oils, and hydrocarbon-type substances. This ester acts as an improving agent for fats and oils and the like, and is useful as a new wax-like material.

(5) The glycolipid methyl ester possesses excellent hydroscopic properties and has a water-retaining ability comparable to that of lanolin and good wet-permeability because of its Sophorose residue. The ester also as wax-like properties because of the presence of the long-chain hydrophobic group. Therefore, when applied as an emulsifying agent, wet-keeping agent or moisturizer for cosmetics, the ester exerts a skin-protecting and feeling-improving effect which cannot be found in the conventional esters.

(6) The glycolipid methyl ester can be easily treated because of its good solubility in water and many organic solvents and is chemically stable. Consequently, the ester finds wide application.

The glycolipid methyl ester of the present invention possesses the above-mentioned superior properties. Therefore, it may be utilized as a base or improving additive for various cleansers, and fats and oils products and for use in painting and printing processes, fiber processing, metal processing, stationery, cosmetics, drugs, agricultural chemicals, luster prevention, synthetic resins, paper manufacturing, machinery, leather and the like.

The invention is illustrated below in further detail with reference to some non-limiting Examples.

EXAMPLE 1

To a mixture of 1,500 g of glucose, 75 g of a yeast extract and 15 g of urea was added water to adjust the whole volume to 15 l, and the resulting mixture was placed in a 30 l fermentor and sterilized, and then utilized as a fermantation liquid. The fermentation liquid was inoculated with 150 ml of a *Torulopsis bombicola* solution which had been cultured on the same medium as above at 30° C. for 48 hours. The fermentation was started with stirring at a speed of 300 rpm and at an aeration of 0.33 VVM at 20° C. Culturing was conducted for 24 hours after the inoculation of the microorganisms, and 150 g of a tallow oil were added at intervals of 24 hours. The added tallow oil amounted to 900 g. After the final addition, the fermentation was continued for 24 hours. The fermentation time amounted to 168 hours. A Sophorolipid layer precipitating at the bottom of the fermentor was collected by decantation to give 1300 g of Sophorolipid in a paste form at room temperature which had a water content of about 50%. To 100 g of the thus obtained Sophorolipid was added 2.5 g of polypropyleneglycol having an average molecular weight of 200, and the resulting mixture was placed in a 300 ml flask equipped with a stirrer and a Liebig condenser. The mixture was evaporated with stirring at 80° C. in an oil bath under a reduced pressure of 250 mmHg to eliminate water. After evaporation for 2 hours, the water content was found to be less than 1% as measured by the Karl Fischer method.

EXAMPLE 2

To a polypropylene glycol solution of Sophorolipid obtained in Example 1 was added 150 g of methanol, and to the resulting mixture was added 2.5 g of sulfuric acid to adjust the whole solution to 0.25 N. The mixture was reacted at 40±2° C. for 90 minutes. The reaction progress was followed by thin layer chromatography on silica gel [solvent: chloroform-methanol-acetic acid (75:20:5)], and the reaction was regarded as having been completed when the many spots shown by the starting material or Sophorolipid converged on the chromatogram. After the completion of the reaction, the sulfuric acid was neutralized with potassium hydroxide, and the reaction solution was filtered through filter paper. The filtrate was placed in a round bottom flask equipped with a Liebig condenser. The methanol and methyl acetate formed were removed by distillation to give 48 g of the residue in a brown paste form which contained polypropyleneglycol and about 94% of a crude glycolipid methyl ester. The glycolipid methyl ester-polypropyleneglycol residue was purified by column chromatography on silica gel, thereby yielding a pure glycolipid methyl ester.

The pure glycolipid methyl ester was a white paste. The infrared absorption spectrum of this product indicated a peak at 1740 cm$^{-1}$ attributable to the ketone group of the ester bond, a broad and strong peak at 3380–3200 cm$^{-1}$ attributable to the hyroxy group of the sugar, and a peak at 900–750 cm$^{-1}$ peculiar to the glycopyranose ring. An NMR spectrum in pyridine as a solvent exhibited various peaks including a group at $\delta$5.5 attributable to the double bond peculiar to the unsaturated fatty acid, broad bond at $\delta$3.5–5.0 attributable to the sugar structure and a group at $\delta$1.1–1.6 attributable to the strong methylene group. Moreover, this product was accertained to be a methyl ester from the following fat analysis: acid value 0, hydroxy value 615, saponification value 88 and ester value 87. The product was refluxed in a hydrochloric acid-methanol solution having a concentration of 5 N to give a methylglycoside and a hydroxyfatty acid methyl ester, which were quantitatively analyzed by gas chromatography. As a result, 2 moles of the methyl glycoside and 1 mole of the hydroxyfatty acid methyl ester were determined. This fact supported the structure of the glycolipid methyl ester.

The glycolipid methyl ester thus obtained had a surface tension of 40 dyne/cm$^2$ and an HLB of more than 20.

EXAMPLE 3

To 100 g of Sophorolipid obtained in Example 1 was added 2.5 g of glycerine, and the resulting mixture was placed in a 300 ml round bottom flask equipped with a stirrer and a Liebig condenser, and evaporated with stirring in an oil bath at 80° C. under a reduced pressure of 250 mmHg to distill off water. After evaporation for 2 hours, the water content was found to be less than 1% as measured by the Karl Fisher method.

Thereafter, the oil bath was cooled to room temperature, and the Liebig condenser was replaced with a reflux condenser. 150 ml of methanol was added. 4.4 g of a 33% hydrochloric acid solution was further added to adjust the whole solution to 0.20 N-HCl, and the resulting mixture was reacted at 40°±2° C. for 90 minutes. The reaction progress was observed by a thin layer chromatogram in the same manner as in Example 2.

After the completion of the reaction, the hydrochloric acid was neutralized with sodium hydroxide, and the reaction solution was filtered through filter paper. The filtrate was placed in a round bottom flask equipped with a Liebig condenser, and the methanol and methyl acetate formed were distilled off. The residue obtained in a yield of 49 g and in a brown paste form contained glycerine and about 94% of a crude glycolipid methyl ester. The glycolipid methyl ester-glycerine residue was purified by column chromatography on silica gel, and a pure glycolipid methyl ester was obtained.

The physicochemical properties of this product were the same as those of the product obtained in Example 2.

EXAMPLE 4

To 100 g of Sophorolipid obtained in Example 1 was added 2.5 g of diethyleneglycol, and the resulting mixture was placed in a 300 ml round bottom flask equipped with a stirrer and a Liebig condenser and heated with stirring in an oil bath at 80° C. under a reduced pressure of 250 mmHg to distill off water. After evaporation for 2 hours, the water content was found to be less than 1% as measured by the Karl Fischer method.

The oil bath was then cooled to room temperature, and the Liebig condenser was replaced with a reflux condenser. Subsequent to the addition of 150 g of methanol, 2.50 g of nitric acid was added to adjust the whole solution to 0.20 N-HNO$_3$, and the resulting mixture was reacted at 40°±2° C. for 90 minutes. The reaction progress was observed in the same manner as in Example 2.

After the completion of the reaction, the nitric acid was neutralized with potassium hydroxide, and the mixture was filtered through filter paper. The filtrate was placed in a round bottom flask equipped with a Liebig condenser, and the methanol and methyl acetate formed were distilled off. The residue obtained in a yield of 49.5 g and in a brown paste form contained diethyleneglycol and about 94% of a crude glycolipid methyl ester. The glycolipid methyl ester-diethyleneglycol residue was purified by column chromatography on silica gel, and there was obtained a pure glycolipid methyl ester.

The physicochemical properties of this product are the same as those of the product obtained in Example 2.

What is claimed as new and intended to be secured by Letters Patent is:

1. A process for producing a glycolipid methyl ester represented by the formula (I),

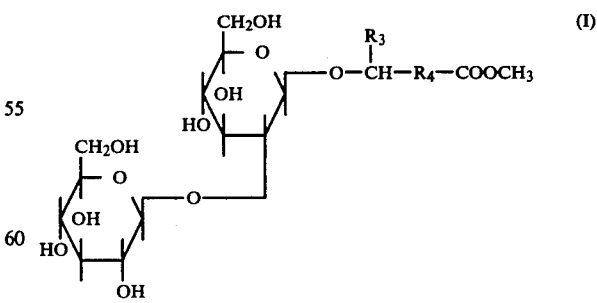

wherein R$_3$ represents hydrogen or methyl, and, R$_4$ represents a staurated or unsaturated hydrocarbon group having 12 to 16 carbon atoms when R$_3$ is hydrogen, and R$_4$ represents a saturated or unsaturated hydrocarbon group having 11 to 15 carbon atoms when R$_3$ is methyl, which comprises mixing at least one polyhydric alcohol represented by formula (III) or (IV),

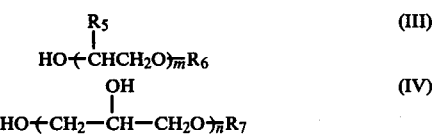

wherein $R_5$ represents hydrogen or methyl, $R_6$ and $R_7$ represent hydrogen or an alkyl group having 1 to 5 carbon atoms, and m and n represent integers from 1 to 6, with hydrated Sophorolipid; removing water by distillation under reduced pressure; and subjecting the resulting Sophorolipid-polyhydric alcohol system to methanolysis and methylation reactions by reaction with methanol in the presence of a strong acid.

2. The process according to claim 1, wherein the strong acid is used in a concentration of from 0.05 to 0.50 N.

3. The process according to claim 1, wherein the methanolysis and methylation reactions are conducted at a temperature below 45° C.

4. The process according to claim 1, wherein said strong acid in nitric acid, sulfuric acid or hydrochloric acid.

5. The process according to claim 1, wherein from 1 to 10 wt. % of said polyhydric alcohol is added to said Sophorolipid.

6. The process according to claim 1, wherein said polyhydric alcohol is ethyleneglycol, ethyleneglycol monomethylether, ethyleneglycol monoethylether, ethyleneglycol monopropyl ether, diethyleneglycol, diethyleneglycol monomethyl ether, diethyleneglycol monoethyl ether, dimethyleneglycol monobutyl ether, polyethyleneglycol having an average molecular weight of 150 to 280, propyleneglycol, dipropyleneglycol, tripropyleneglycol, tetrapropyleneglycol, pentapropyleneglycol, hexapropyleneglycol, propyleneglyol monomethyl ether, propyleneglycol monoethyl ether, propyleneglycol monopropyl ether, propyleneglycol monobutyl ether, dipropyleneglycol monomethyl ether, dipropyleneglycol monoethyl ether, or tripropyleneglycol monomethyl ether.

7. The process according to claim 1, wherein said polyhydric alcohol is glycerine, polyglycerine, or blockpolymers of ethylene glycol and propyleneglycol.

* * * * *